(12) United States Patent
Levine et al.

(10) Patent No.: US 8,168,391 B2
(45) Date of Patent: May 1, 2012

(54) METHOD FOR MODULATING INSULIN PRODUCTION

(75) Inventors: Fred Levine, Del Mar, CA (US); Pamela Itkin-Ansari, Carlsbad, CA (US); Mark Mercola, Del Mar, CA (US)

(73) Assignees: Burnham Institute for Medical Research, La Jolla, CA (US); The Regents of the University of California, Oakland, CA (US)

(*) Notice: Subject to any disclaimer, the term of this patent is extended or adjusted under 35 U.S.C. 154(b) by 629 days.

(21) Appl. No.: 12/267,507

(22) Filed: Nov. 7, 2008

(65) Prior Publication Data
US 2009/0137543 A1 May 28, 2009

Related U.S. Application Data

(60) Provisional application No. 60/986,239, filed on Nov. 7, 2007.

(51) Int. Cl.
C12Q 1/68 (2006.01)
G01N 33/53 (2006.01)
G01N 33/567 (2006.01)
C12N 15/00 (2006.01)
(52) U.S. Cl. ..... 435/6.13; 435/7.1; 435/7.21; 435/320.1
(58) Field of Classification Search ............. 435/6.13, 435/7.1, 7.21, 320.1, 354
See application file for complete search history.

(56) References Cited

U.S. PATENT DOCUMENTS

| 7,910,305 B2 * | 3/2011 | Mercola et al. ............. 435/6.13 |
| 2006/0069161 A1 | 3/2006 | Lee et al. |

FOREIGN PATENT DOCUMENTS

| EP | 0 440 333 A2 | 8/1991 |
| EP | 1 782 832 A1 | 5/2007 |
| WO | WO 93/12793 A1 | 7/1993 |
| WO | WO 97/41873 A1 | 11/1997 |
| WO | WO 98/17306 A1 | 4/1998 |
| WO | WO 2007/035546 A2 | 3/2007 |

OTHER PUBLICATIONS

Bonner-Weir et al., "In Vitro Cultivation of Human Islets from Expanded Ductal Tissue", *PNAS*, 97(14):7999-8004, 2000.
Hao et al., "Beta-Cell Differentiation From Nonendocrine Epithelial Cells of the Adult Human Pancreas", *Nature Medicine* 12(3):310-316, 2006.
Odagiri et al., "Function of the Human Insulin Promoter in Primary Cultured Islet Cells", *Journal of Biological Chemistry*, 271(4):1909-1915, 1996.
Yoshimura et al "Continuous Carbachol Infusion Promotes Peripheral Cell Proliferation and Mimics Vagus Hyperactivity in a Rat Model of Hypothalamic Obesity", *Biomedical Research* 27(2):81-88, 2006.

Ammon and Steinke, "Apparent Biphasic Action of Chlorpromazine on Insulin Release from Isolated Pancreatic Rat Islets", *Diabetes*, 20(suppl. 1):345-346 (1971).
Bian et al. "Synthesis and antihyperglycemic evaluation of various protoberberine derivatives", *Bioorg. Med. Chem. Lett.*, 16(5).1380-1383 (2006).
Database WPI, Week 200342, Thomson Scientific, London, GB, AN 2003-442171, XP002609751, & CN 1 393 264 A (Jiang J), Jan. 29, 2003. Abstract.
Database WPI, Week 200379, Thomson Scientific, London, GB, AN 2003-854355, XP002609750, & WO 03/090749 A1 (Wu K), Nov. 6, 2004. Abstract.
Database WPI, Week 200431, Thomson Scientific, London, GB, AN 2004-340813, XP002609749, & WO 2004/032924 A1 (Jiang J), Apr. 22, 2004. Abstract.
Database WPI, Week 200457, Thomson Scientific, London, GB, AN 2004-581709, XP002609748, & CN 1 493 286 A (Kong F), May 5, 2006, Abstract.
Database WPI, Week 200608, Thomson Scientific, London, GB, AN 2006-068506, XP002609753, & CN 1 651 433 A (Univ. Shandong), Aug. 10, 2005, Abstract.
Database WPI, Week 200676, Thomson Scientific, London, GB, AN 2006-730960, XP002609747, & CN 1 788 726 A (Zhejiang Kinisy Pharm Co. LTD), Jun. 21, 2006. Abstract.
Database WPI, Week 200736, Thomson Scientific, London, GB, AN 2007-376871, XP002609752, & CN 1 872 852 A (Univ. Affiliated Tongji Hospital Tongji M), Dec. 6, 2006. Abstract.
de Leeuw van Weenen et al., "The dopamine receptor D2 agonist bromocriptine inhibits glucose-stimulated insulin secretion by direct activation of the alpha2-adrenergic receptors in beta cells", *Biochem. Pharmacol.*, 79(12):1827-1836 (2010).
Ei-Denshary and Montague, "Effects of drugs on glucose and tolbutamide-stimulated insulin release from isolated rat islets of Langerhans", *Biochem Pharmacol.*, 25(13):1451-1454 (1976).
Erle et al., "Effect of chlorpromazine on blood glucose and plasma insulin in man", *Eur. J. Clin. Pharmacol.*, 11(1):15-18 (1977).
Federspil et al., "Chlorpromazine in the treatment of endogenous organic hyperinsulinism", *Diabetologia.*, 10(3):189-191 (1974).
Joost H.G., "Inhibition of insulin secretion from the perfused pancreas of the rat by pizotifen", *Br. J. Pharmacol.*, 67(2):265-267 (1979).
Kiselyuk et al., "Phenothiazine neuroleptics signal to the human insulin promoter as revealed by a novel high-throughput screen", *J. Biomol. Screen.*, 15(6):663-670 (2010).
Ko et al., "Insulin sensitizing and insulinotropic action of berberine from Corditis rhizoma", Department of Food and Nutrition, Hoseo University, Asan, Chungnam-do, 336-795 Korea, *Biological & Phamaceutical Bullitin*. 28(8):1431-1437 (2005).
Lee et al., "Berberine, a natural plant product, activates AMP-activated protein kinase with beneficial metabolic effects in diabetic and insulin-resistant states", *Diabetes*, 55(8):2256-2264 (2006).

(Continued)

*Primary Examiner* — Kevin E Weddington
(74) *Attorney, Agent, or Firm* — DLA Piper LLP (US)

(57) ABSTRACT

The present invention provides screening methods for the detection of agents that affect various aspects of β-cell biology, particularly insulin gene expression. Screening methods are also provided for detection of agents that affect β-cell differentiation from progenitor cells. Additionally, agents identified using such methods are provided and are useful for increasing insulin gene expression and reducing lipotoxicity.

11 Claims, 18 Drawing Sheets

OTHER PUBLICATIONS

Leng et al., "Therapeutic effects of berberine in impaired glucose tolerance rats and its influence on insulin secretion", *Acta. Pharmacol. Sin.*, 25(4):496-502 (2004).

Nakadate et al., "Effect of chlorpromazine on insulin release in mice: comparison between in vivo and in vitro", *Jpn. J. Pharmacol.*, 32(5):950-953 (1982).

Nogueira et al., "Modulation of insulin secretion and 45Ca2+ efflux by dopamine in glucose-stimulated pancreatic islets", *Gen. Pharmacol.*, 25(5):909-916 (1994).

Park et al., "Chlorpromazine exacerbates hepatic insulin sensitivity via attenuating insulin and leptin signaling pathway, while exercise partially reverses the adverse effects", *Life Sci.*, 80(26):2428-2435 (2007).

Rubl et al., "Dopamine D2-like receptors are expressed in pancreatic beta cells and mediate inhibition of insulin secretion", *J. Biol. Chem.*, 280(4):36824-36832 (2005).

Shankar et al., "Dopaminergic regulation of glucose-induced insulin secretion through dopamine D2 receptors in the pancreatic islets in vitro", *IUBMB Life.*, 58(3):157-163 (2006).

Wang et al., "Effect of berberine on insulin secretion and glucokinase activity of NIT-1 cells", *Acta Pharmaceutica Sinica* (Yao Xue Xue Bao), 42(10):1045-1049 (2007). Abstract.

European Search Report (ESR) from EP 08 84 7400, (2000).

* cited by examiner

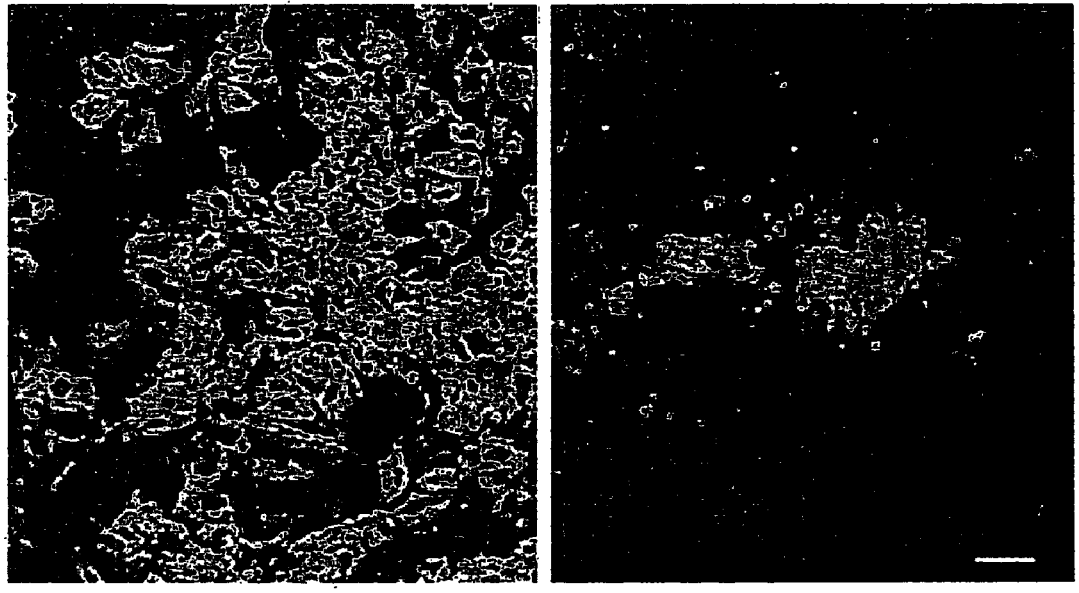
FIG. 5A  FIG. 5B
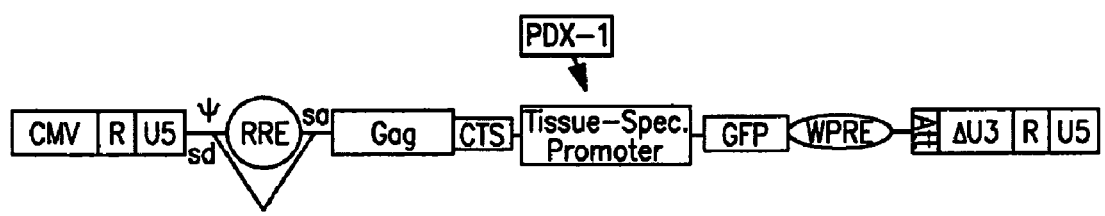
FIG. 6

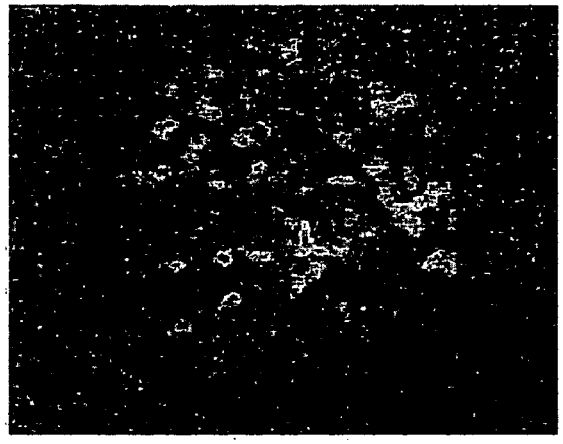 
FIG. 9A  FIG. 9B
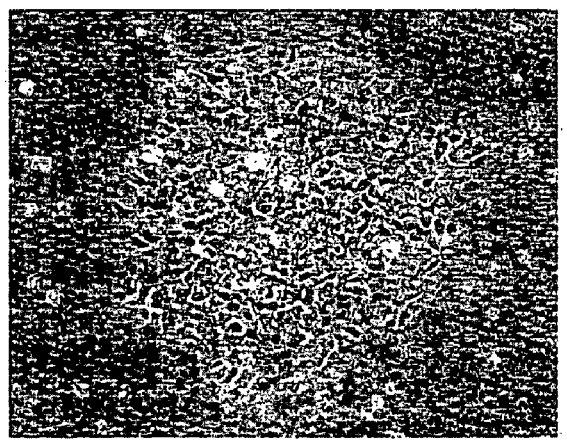 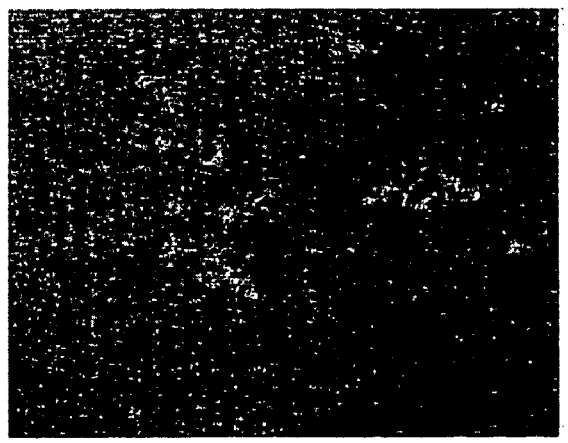
FIG. 10A  FIG. 10B

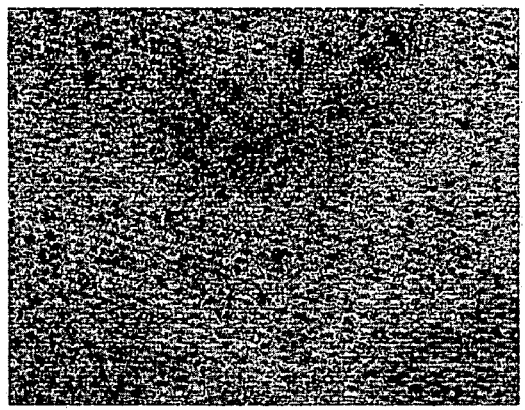
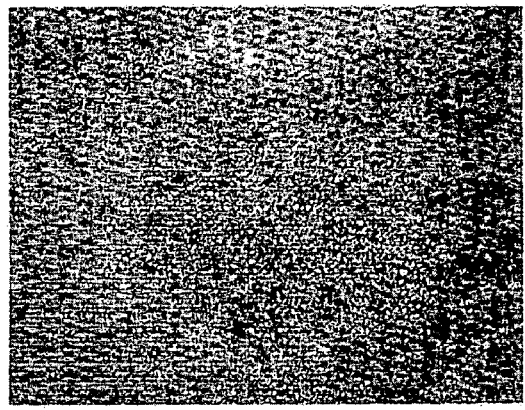
FIG. 11A  FIG. 11B
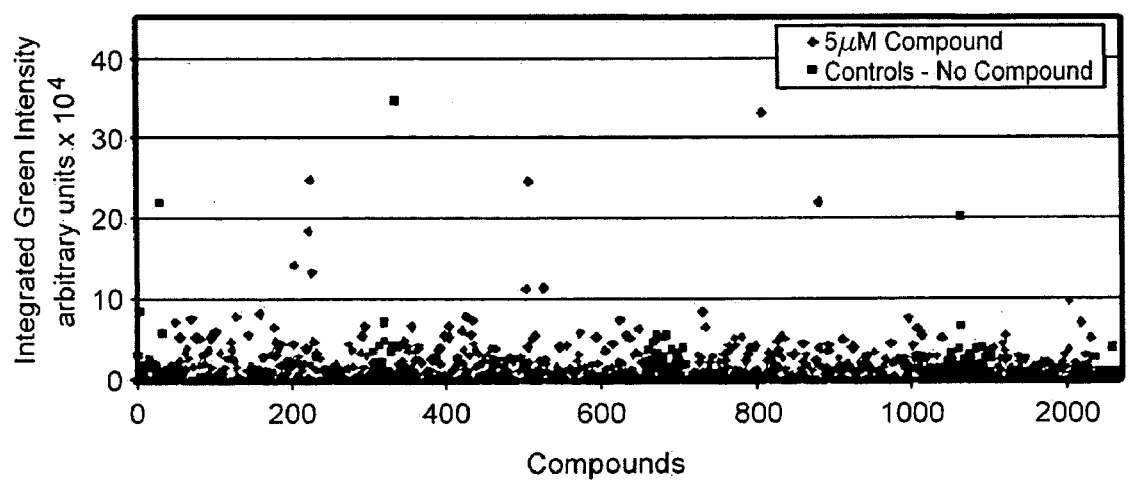
FIG. 12

METHOD FOR MODULATING INSULIN PRODUCTION

CROSS REFERENCE TO RELATED APPLICATION(S)

This application claims the benefit of priority under 35 U.S.C. §119(e) of U.S. Ser. No. 60/986,239, filed Nov. 7, 2007, the entire content of which is incorporated herein by reference.

GRANT INFORMATION

This invention was made with government support under NIH Grant No. 3R01 DK055283-08S1 awarded by the National Institutes of Health. The government has certain rights in the invention.

BACKGROUND OF THE INVENTION

1. Field of the Invention

The present invention relates generally to the field of β-cell physiology and more specifically to the identification of agents that modulate insulin expression and production.

2. Background Information

Diabetes mellitus is a familiar disease well known to lead to morbidity and mortality. Diabetes is characterized by high blood glucose levels, which result from defects in insulin production, insulin action, or both. Both genetics and environmental factors, such as obesity and lack of exercise, are known factors contributing to pathology of the disease.

There are two primary types of diabetes, Types I and II. Type I, or insulin-dependent diabetes mellitus (IDDM) or juvenile-onset diabetes is due to autoimmune destruction of insulin-producing β-cells in the pancreatic islets. Type I usually occurs in childhood or young adults. However the disease may occur at any age. Treatments options typically include daily injections of insulin, combined with frequent testing of blood glucose levels to guide adjustment of insulin doses.

Type II, or noninsulin-dependent diabetes mellitus (NDDM) or adult-onset diabetes typically develops in adulthood and is characterized as a metabolic disorder resulting from the body's inability to make enough, or properly use, insulin. NDDM is associated with resistance of glucose-utilizing tissues like adipose tissue, muscle, and liver, to the actions of insulin. Type II diabetes usually begins as insulin resistance, a disorder in which the cells do not use insulin properly, and as the need for insulin rises, the pancreas gradually loses its ability to produce insulin. Type 2 diabetes is the most common form of the disease accounting for 90-95 percent of diabetes.

A third type of diabetes is known as gestational diabetes. This disease is linked to glucose intolerance as diagnosed in pregnant women.

Other disorders associated with diabetes include hyperinsulinemia, which refers to the overproduction of insulin by pancreatic cells. Hyperinsulinemia usually results from insulin resistance, a condition characterized by cellular resistance to the action of insulin. Insulin resistance, is characterized when a normal amount of insulin produces a subnormal biologic (metabolic) response. Additionally, lipotoxemia is a process characterized by the accumulation of excess fatty acids accompanied by triglyceride in parenchymal cells of multiple tissues including skeletal and cardiac myocytes, hepatocytes, and pancreatic beta cells resulting in chronic cellular dysfunction and injury.

The insulin promoter is the target of diabetogenic molecules, such as fatty acids, which play a role in the onset and characterization of diabetes. As such, innovative screening methods are needed to identify new agents that may be useful for the treatment and prevention of diabetes and related disorders.

SUMMARY OF THE INVENTION

The present invention is based in part on screening methods for identification of agents that affect various aspects of β-cell biology, particularly insulin gene expression. Additionally, the present invention provides agents useful for increasing insulin expression, thereby increasing insulin production.

Accordingly, in one embodiment, the present invention provides a method of inducing or increasing insulin expression. The method includes administering to a subject in need thereof a therapeutically effective dose of a composition including berbamine, ethopropazine, chlorpromazine, a dopamine agonist, or an analog thereof, or combination thereof thereby increasing the insulin expression in the subject. In one aspect, the subject suffers from Type I or Type II diabetes. In another aspect, exogenous insulin is also administered to the subject prior to, simultaneously with or following administration of the composition.

In another embodiment, the invention provides a method of reducing lipotoxicity in a subject having Type I or Type II diabetes. The method includes administering to the subject a composition including a class of drug selected from the group consisting of a fatty acid metabolism modulator, anti-inflammatory, antioxidant, neuroleptic, cholinergic, adrenergic, antitussive, antibiotic, and antiarrhythmic, or a combination thereof. In one aspect, the drug is a HMGCoA reductase inhibitor, benfluorex hydrochloride, triameinolone acetonide, dexamethasone acetate, mefenamic acid, beta carotene, alpha tocopheryl acetate, cloperastine hydrochloride, or ipratropium bromide monohydrate. In another aspect, exogenous insulin is also administered to the subject prior to, simultaneously with or following administration of the composition.

In another embodiment, the present invention provides a method of screening for agents that activate β-cell differentiation of progenitor cells. The method includes transfecting cells with a vector including a tissue specific promoter, such as a pancreatic tissue specific promoter, operably linked to a nucleic acid encoding a reporter protein. The cell is then contacted with a test compound and the level of expression of the reporter protein is detected. The level of expression of the reporter protein detected serves as an indicator of β-cell Differentiation of progenitor cells. An increase in expression of the reporter protein indicates up-regulation or activation of the tissue specific promoter by the test agent, thus identifying the test agent as an agent that activates β-cell differentiation of progenitor cells. In one aspect, the pancreatic tissue specific promoter is a PDX-1 promoter. In exemplary aspects, the progenitor cell is an adult non-endocrine epithelial pancreas cell. Agents include but are not limited to proteins, peptides, nucleic acid, small molecule chemical compounds, and the like.

Accordingly, in one aspect, the present invention provides a method of screening for agents that activate insulin expression. The method includes transfecting cells with a vector that includes an insulin promoter operably linked to a nucleic acid encoding a reporter protein. The cell is then contacted with a test compound and the level of expression of the reporter protein is detected. The level of expression of the reporter protein serves as an indicator of insulin promoter activation by the test compound. An increase in expression of the reporter protein indicates up-regulation or activation of the insulin promoter by the test agent, thus identifying the test agent as an activator of insulin expression. In one aspect, the reporter protein is a fluorescent molecule, such as a green fluorescent protein (e.g., eGFP).

In another aspect, the present invention provides a method of screening for agents that reduce lipotoxicity in a subject suffering from Type I or Type II diabetes. The method includes transfecting cells with a vector that includes an insulin promoter operably linked to a nucleic acid encoding a reporter protein. The cell is then contacted with a test compound and the level of expression of the reporter protein is detected. The level of expression of the reporter protein serves as an indicator of insulin promoter activation by the test compound. An increase in expression of the reporter protein indicates up-regulation or activation of the insulin promoter by the test agent. In one aspect, the reporter protein is enhanced green fluorescent protein (eGFP).

BRIEF DESCRIPTION OF THE DRAWINGS

FIG. 5 shows a pictorial representation of tissue specific expression of PDX-1 in maturing pancreatic β-cells differentiated from duct cells. FIG. 5A shows differentiating duct cells immunostained with antibodies directed to pancytokeratin and insulin. FIG. 5B shows differentiating duct cells immunostained with antibodies directed to PDX-1 and insulin.

FIG. 6 shows a pictorial representation of a promoter/reporter construct generated from a modified viral vector used to infect cells in the present invention.

FIG. 9 shows pictorial representations of NEPCs infected with viral vector constructs followed by plating and growth for 3.5 days and subsequent replating and growth for 1 additional day. Image analysis using fluorescence microscopy with detection of eGFP is shown at 3.5 days in FIG. 9A and after replating and growth for 1 additional day in FIG. 9B.

FIG. 10 shows pictorial representations of NEPCs plated and grown for 3.5 days and subsequent replating and growth for 1 additional day before detection of using bight field microscopy. FIG. 10A shows the cells at 3.5 days and FIG. 10B shows the cells after plating and growth for 1 additional day.

FIG. 11 shows pictorial representations of NEPCs cultured without supplementation with 10% plasma (FIG. 11A) and with supplementation of 10% plasma (FIG. 11B).

FIG. 12 shows a graphical representation of screening results for identification of regulators of insulin gene transcription.

DETAILED DESCRIPTION OF THE INVENTION

Figure 1:
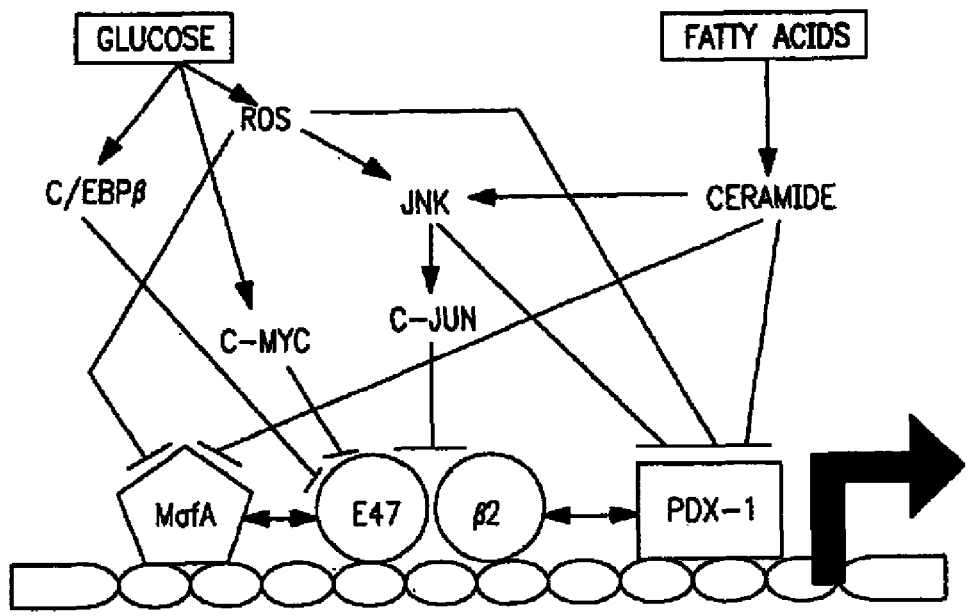
FIG. 1 shows a pictorial representation of the inhibitory effects of fatty acids on insulin transcription.

The present invention is based in part on novel screening methods allowing for the detection of agents that affect various aspects of β-cell biology, particularly insulin gene expression, as well as agents identified using such methods.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the terms "sample" and "biological sample" refer to any sample suitable for the methods provided by the present invention. The sample can be any sample that may be used such that insulin promoter activity can be detected. In one aspect, the sample is a biological sample, including, for example, a bodily fluid, an extract from a cell, which can be a crude extract or a fractionated extract, a chromosome, an organelle, or a cell membrane; a cell; genomic DNA, RNA, or cDNA, which can be in solution or bound to a solid support; a tissue; or a sample of an organ. A biological sample, for example, from a human subject, can be obtained using well known and routine clinical methods (e.g., a biopsy procedure).

The present invention describes agents, such as chemical compounds, and the processes and assays used for their identification, that modulate insulin and PDX-1 (Pancreatic and duodenal homeobox 1) expression by affecting promoter activity. Such compounds are expected to be useful in prevention and treatment of diabetes and other diseases related to regulation of insulin, such as lipotoxemia. Accordingly, in one aspect, the present invention provides a method of screening for agents that activate insulin expression, the method includes transfecting cells with a vector that includes an insulin promoter operably linked to a nucleic acid encoding a reporter protein. The cell is then contacted with a test compound and the level of expression of the reporter protein is detected. The level of expression of the reporter protein serves as an indicator of insulin promoter activation by the test compound. An increase in expression of the reporter protein indicates up-regulation or activation of the insulin promoter by the test agent, thus identifying the test agent as an activator of insulin expression. In one aspect, the reporter protein is eGFP.

As used herein, an agent identified as an activator of transcription acts to increase transcription of the gene of interest, such as insulin or PDX-1. The agent may interact directly with the promoter sequence to effectuate an increase in transcription or the agent may interact in a number of other ways to indirectly stimulate transcription. For example, the agent may bind to cell surface receptors to activate a particular signal transduction pathway leading to increased transcription of the gene. Alternatively, the agent may act to suppress repressors of insulin transcription by direct binding to the transcriptional repressor thus blocking binding of the repressor to the promoter. Alternatively, the agent may act indirectly to suppress transcriptional repressors or increase transcription.

Figure 2:
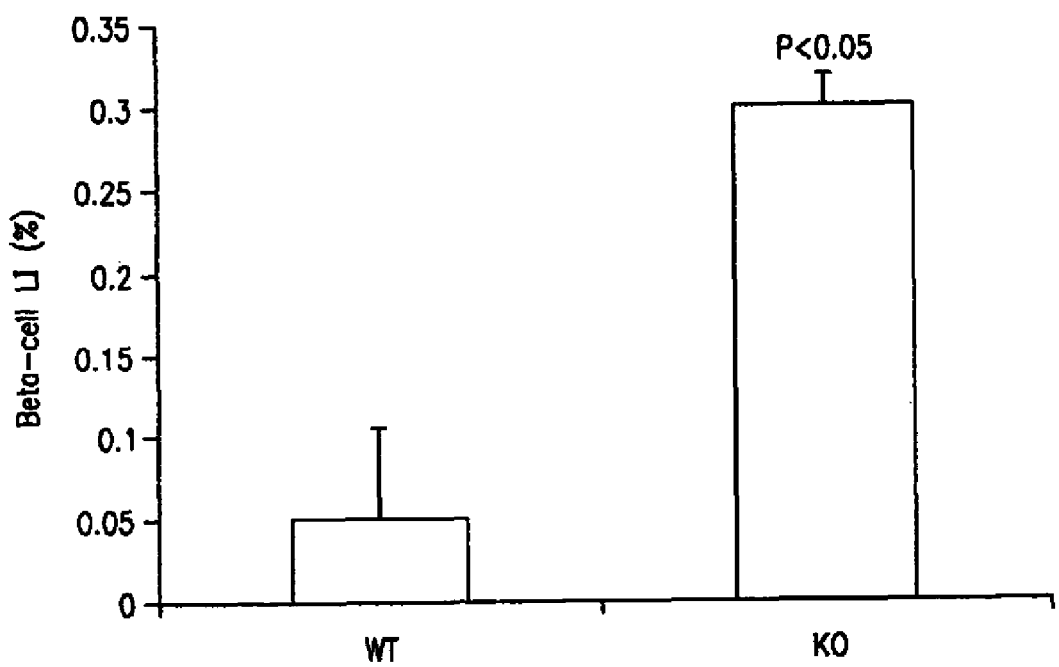
FIG. 2 shows a graphical representation of the increased, β-cell labeling index, a measure of cell survival and propagation, of Hes6 mutants as compared to wild type.

In another aspect, the present invention provides a method of screening for agents that reduce lipotoxicity in a subject. Lipotoxemia is a process characterized by the accumulation of excess fatty acids accompanied by triglyceride in parenchymal cells of multiple tissues including skeletal and cardiac myocytes, hepatocytes, and pancreatic beta cells resulting in chronic cellular dysfunction and injury. As shown in FIG. 1, lipotoxeniia or lipotoxicity affects insulin production. It has been determined that fatty acids acting through reactive oxygen species can have a deleterious effect on insulin expression by inhibiting promoter activation. Additionally lipotoxicity is related to regeneration of β-cells. This is evidenced by the increase of proliferation in Hes6 mutants on a high fat diet. Hes6 is a transcription factor that inhibits transcriptional repression by Hes1. The β-cells of the mutants have been shows to express Ki-67, insulin and amylase. FIG. 2 shows the increase in β-cell labeling index, a measure of cell survival and propagation, observed with Hes6 mutants as compared to wild type. This indicates that pathways are involved downstream of fat processing in which Notch signaling is being interacted to promote β-cell replication.

Figure 3:
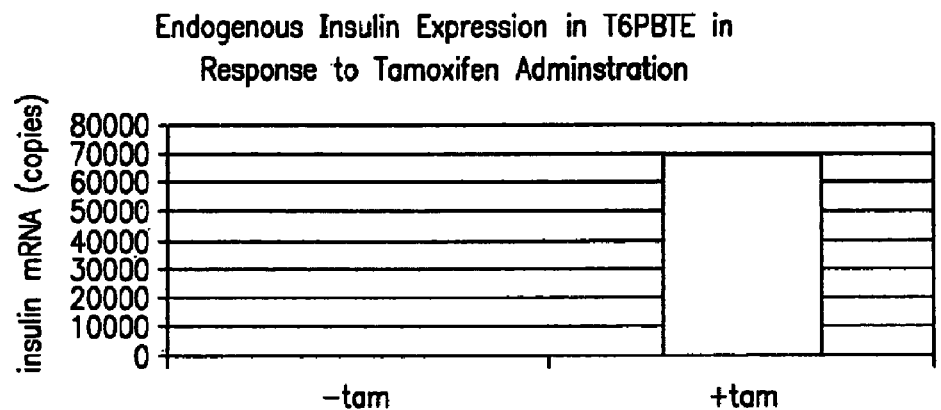
FIG. 3 shows a graphical representation of the endogenous expression of insulin in response to tamoxifen administration in a cell line derived from fetal islet cells (T6PBTE).
Figure 4:
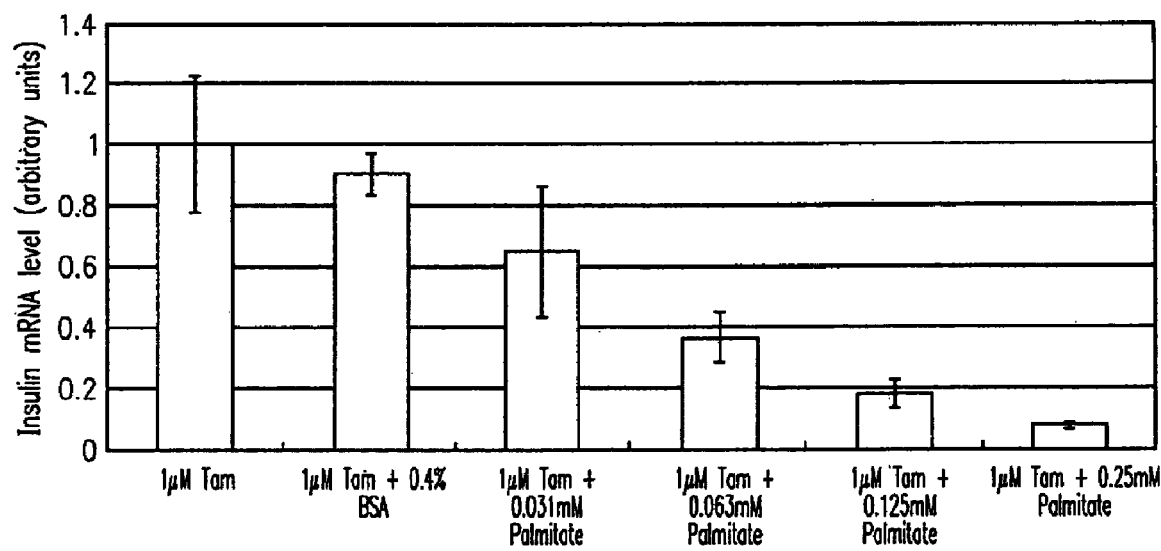
FIG. 4 shows a graphical representation of the reduction in transcription of insulin in response to the fatty acid palmitate.

Lipotoxicity has been shown to have a dramatically reducing effect on expression of the insulin gene. FIG. 3 shows the endogenous expression of insulin in response to tamoxifen administration in a cell line derived from fetal islet cells (T6PBTE). However, in the presence of a fatty acid, such as palmitate, the endogenous expression of insulin is dramatically reduced as shown in FIG. 4. Thus, employing the appropriate screening methods of the present invention, agents may be identified that are capable of reversing or reducing the effects of lipotoxicity on the insulin promoter.

Accordingly, in another aspect, the present invention provides a method of screening for agents that reduce lipotoxicity in a subject suffering from Type I or Type II diabetes. The method includes transfecting cells with a vector that includes an insulin promoter operably linked to a nucleic acid encoding a reporter protein. The cell is then contacted with a test compound and the level of expression of the reporter protein is detected. The level of expression of the reporter protein serves as an indicator of insulin promoter activation by the test compound. An increase in expression of the reporter protein indicates up-regulation or activation of the insulin promoter by the test agent.

Additional screening approaches to identify agents that specifically act to reverse or reduce lipotoxicity as compared to generally increasing transcription of insulin have been developed. For example, the high throughput screening (HTS) methods of the present invention may incorporate a two tier screening approach. In the first tier, islet cells infected with an insulin promoter/reporter construct are screened in the absence of a fatty acid. A "hit" indicates an agent that is capable of increasing insulin transcription. In the second tier, islet cells infected with an insulin promoter/reporter construct are screened in the presence of a fatty acid. A "hit" indicates a drug that reverses the effects of the fatty acid addition, for example reduction of insulin transcription. Thus drugs screened in both layers may be used to identify whether the drug is specific to lipotoxicity reversal or reduction. For example, drugs that are "hits" in the second tier screen but not in the first screen are specific to lipotoxicity reversal.

PDX-1 (Pancreatic and duodenal homeobox 1), also known as insulin promoter factor 1, is a transcription factor necessary for pancreatic development and β-cell maturation. PDX-1, otherwise known as Ipf1, is the human gene that encodes the transcription factor. PDX-1 is necessary for β-cell maturation from duct cells to mature endocrine cells. It is known that developing β-cells co-express PDX-1, NKX6-1, and insulin, resulting in the maturation of β-cells. Accordingly, PDX-1 expression is tissue specific and it therefore serves as a convenient tissue specific marker for β-cell differentiation and/or endocrine differentiation in duct cells as shown in FIG. 5 which shows endocrine differentiation in duct cells using PDX-1 as the marker.

Accordingly, in another aspect, the present invention provides a method of screening for agents that activate β-cell differentiation of progenitor cells. The method includes transfecting cells with a vector including a pancreatic tissue specific promoter operably linked to a nucleic acid encoding a reporter protein. The cell is then contacted with a test compound and the level of expression of the reporter protein is detected. The level of expression of the reporter protein detected serves as an indicator of β-cell differentiation of progenitor cells. An increase in expression of the reporter protein indicates up-regulation or activation of the tissue specific promoter by the test agent, thus identifying the test agent as an agent that activates β-cell differentiation of progenitor cells. In one aspect, the pancreatic tissue specific promoter is a PDX-1 promoter. In exemplary aspects, the progenitor cell is an adult non-endocrine epithelial pancreas cell.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

The terms "small interfering RNA" and "siRNA" also are used herein to refer to short interfering RNA or silencing RNA, which are a class of short double-stranded RNA molecules that play a variety of biological roles. Most notably, siRNA is involved in the RNA interference (RNAi) pathway where the siRNA interferes with the expression of a specific gene. In addition to their role in the RNAi pathway, siRNAs also act in RNAi-related pathways (e.g., as an antiviral mechanism or in shaping the chromatin structure of a genome).

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

An agent useful in any of the methods of the invention can be any type of molecule, for example, a polynucleotide, a peptide, a peptidomimetic, peptoids such as vinylogous peptoids, chemical compounds, such as organic molecules or small organic molecules, or the like, and can act in any of various ways to activate expression of insulin. Accordingly, in one aspect, an agent identified by the method of the present invention is a chemical compound. For example the agent is a chemical compound identified using the assays describe herein, such as but not limited to a HMGCoA reductase inhibitor, benfluorex hydrochloride, triamcinolone acetonide, dexamethasone acetate, mefenamic acid, beta carotene, alpha tocopheryl acetate, cloperastine hydrochloride, ipratropium bromide monohydrate. Additionally, the compound may be a drug classified in one or more of the following classes of drugs: fatty acid metabolism, anti-inflammatory, antioxidant, neuroleptic, cholinergic, adrenergic, antitussive, antibiotic, and antiarrhythmic.

Compounds of the invention can be modified and derivatized at multiple functional groups to enhance pharmacokinetic, pharmacodynamic, and biochemical properties. Such methods are commonly known to those of skill in the art.

Test agents encompass numerous chemical classes, though typically they are chemical compounds, such as an organic molecule, and often are small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The screening methods of the present invention may employ vectors including the entire gene of interest of which expression is to be determined, or any portion thereof, such as the promoter. A "promoter" is a nucleic acid sequence that directs the binding of RNA polymerase and thereby promotes RNA synthesis. Promoter sequences include constitutive and inducible promoter sequences. In various aspects, exemplary promoter sequences may include pancreatic tissue specific promoters, such as but not limited to PDX-1, or an insulin promoter. The promoters can be either naturally occurring promoters, hybrid promoters, or synthetic promoters. Hybrid promoters, which combine elements of more than one promoter, are also known in the art, and are useful in the present invention.

The vectors employed in the present invention may include a reporter gene/protein or reporter molecule to facilitate detecting the transcriptional activity of the gene of interest, such as the insulin gene or PDX-1. For example, the present invention contemplates construction of promoter/reporter constructs. There are many genes and molecules that may be used in such a fashion, as well as methods of labeling known to those of ordinary skill in the art. Examples of the types of reporters known in the art includes radionuclides, enzymes, fluorescent, chemiluminescent, or chromogenic agents as well as substrates, cofactors, inhibitors, or magnetic particles. The reporter molecule or gene can be visibly observable or detectable using conventional detection techniques. In one embodiment promoter/reporter construct includes a promoter operably linked to a reporter gene encoding a protein, such as green fluorescent protein (GFP) originally isolated from the jellyfish *Aequorea victoria*, or recombinantly produced enhanced GFP (eGFP).

Figure 7:
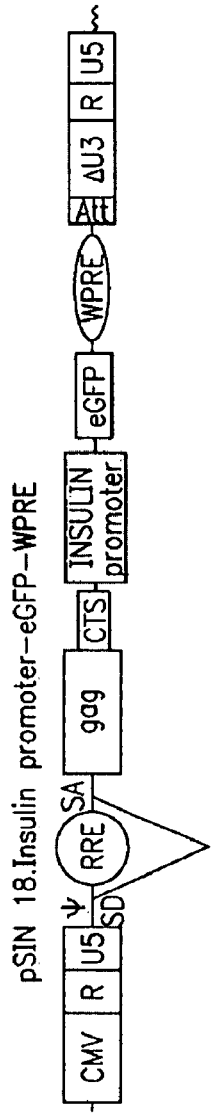
FIG. 7 shows a pictorial representation of a promoter/reporter construct generated from a modified viral vector used to infect cells in the present invention.

An illustrative example is a viral vector construct for infection of cells includes a PDX-1 promoter operably linked to eGFP as shown in FIG. 6, in which a modified viral vector is shown that is used to infect non-endocrine pancreatic cells (NEPCs). Infected NEPCs may be cultured in a multiwell format suitable for high throughput screening (HTS), such as 384 well microtiter plate format, contacted with a test agent, and then analyzed to detect the level of reporter gene (i.e., eGFP) expression to identify agents that increase expression of the construct by activation of the promoter. Another illustrative example is a viral vector construct including an insulin promoter operably linked to eGFP as shown in FIG. 7, in which a modified viral vector is shown that is used to infect non-endocrine pancreatic cells (NEPCs).

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used for expression, as will be appreciated by those in the art. Numerous types of appropriate expression vectors, and suitable regulatory sequences are known in the art for a variety of host cells.

However, detection of the transcriptional activity of the promoter of interest need not be through a promoter/reporter construct. For example, the transcriptional activity may be detected using other methods well known in the art, such as monitoring the activity utilizing GeneChip™ platforms to monitor expression profiles and transcriptional activity. Accordingly, the MBD protein-mediated gene is not required to include a reporter.

The screening method of the present invention may be performed on a number of platforms and utilize a variety of cell types. The method of the present invention may be performed, for example, on a solid support platform, or may be performed using a cell based assay. A variety of cells may be used, those known in the art and those commercially available, as well as those isolated from a subject. In an exemplary aspect pancreatic cells or pancreatic progenitor cells are utilized. For example, non-endocrine epithelial cells (NEPCs) or cells derived from human fetal islet cells (i.e., cell line T6PNE or T6PBTE) are utilized. Additionally, the method may be performed using cells transfected with a promoter/reporter construct, such as described in the Examples and FIGS. 6 and 7. As such, the method is particularly suited to be performed in a high-throughput fashion, (i.e., 96 or 384-well plate analysis; mechanical or robotic processing).

The screening strategy of the present invention may employ chimeric polypeptides containing an affinity or epitope tag, such as a poly-His, GST, HA, Flag, myc, CBP, CYD (covalent yet dissociable NorpD peptide), HPC (heavy chain of protein C) peptide tags, MBP, or other tag well known in the art. Such tags allow proteins to be conveniently isolated and purified through the interaction of the affinity or epitope tag with a cognate binding species, which can be a metal ion, glutathione, anti-HA antibody, anti-Flag antibody or anti-myc antibody, respectively, for the tags listed above. Furthermore, the affinity tag can be used to anchor the polypeptide to a solid support, such as a nickel-resin in the case of a His-tagged protein. Also contemplated by the invention are tags or other modifications that may be added to a protein post-synthetically. For example, a peptide can be biotinylated for affinity purification and immobilization using avidin or streptavidin reagents. In various embodiments, the reporter protein is luciferase (LUC), β-lactamase, chloramphenicol acetyltransferase (CAT), adenosine deaminase (ADA), aminoglycoside phosphotransferase (neo, G418), dihydrofolate reductase (DHFR), hygromycin-B-phosphotransferase (HPH), thymidine kinase (TK), β-galactosidase (β-gal), and xanthine guanine phophoribosyltransferase (XGPRT), an affinity or epitope tag, or a fluorescent protein. In exemplary embodiments, the reporter protein is GFP or eGFP.

The green fluorescent protein (GFP) is composed of 238 amino acids (26.9 kDa), originally isolated from the jellyfish *Aequorea victoria* that fluoresces green when exposed to blue light. Enhanced green fluorescent protein (eGFP) is a 29 kDa recombinantly produced protein with Ex/Em=488/507 nm derived from GFP including mutations such as, the (F64L) point mutation to enhance fluorescence.

A number of additional fluorescent proteins are known in the art and suitable for use with the present invention, including but not limited to blue fluorescent proteins (e.g., EBFP, EBFP2, Azurite, mKalama1), cyan fluorescent proteins (e.g., ECFP, Cerulean, CyPet) and yellow fluorescent proteins (e.g., YFP, Citrine, Venus, YPet).

The agents identified by the screening methods described herein, may be useful for reversing or reducing lipotoxicity or increasing insulin expression in a subject. As such, in one embodiment, the present invention provides a method of inducing or increasing insulin expression in a subject in need thereof. The method includes administering to the subject a therapeutically effective dose of a composition including an agent identified by the screening methods described herein shown to be an activator of insulin transcription. In one aspect, the agent is berbamine, ethopropazine, chlorpromazine, a dopamine agonist, or an analog thereof which have been shown to be activators of insulin transcription in pancreatic cells. The compounds may be administered to prevent or treat subjects suffering from Type I or Type II diabetes.

In another embodiment, the invention provides a method of reducing lipotoxicity in a subject having Type I or Type II diabetes. The method includes administering to the subject a therapeutically effective dose of a composition including an agent identified by the screening methods described herein shown to selectively reverse or reduce lipotoxicity. In one aspect, the agent is a drug from the following classes of drugs: fatty acid metabolism, anti-inflammatory, antioxidant, neuroleptic, cholinergic, adrenergic, antitussive, antibiotic, and antiarrhythmic. In another aspect, the drug is a HMGCoA reductase inhibitor, benfluorex hydrochloride, triamcinolone acetonide, dexamethasone acetate, mefenamic acid, beta carotene, alpha tocopheryl acetate, cloperastine hydrochloride, or ipratropium bromide monohydrate.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The route of administration of a composition containing an agent as identified herein, will depend, in part, on the chemical structure of the molecule. Polypeptides and polynucleotides, for example, are not particularly useful when administered orally because they can be degraded in the digestive tract. However, methods for chemically modifying polynucleotides and polypeptides, for example, to render them less susceptible to degradation by endogenous nucleases or proteases, respectively, or more absorbable through the alimentary tract are well known. For example, a peptide agent can be prepared using D-amino acids, or can contain one or more domains based on peptidomimetics, which are organic molecules that mimic the structure of peptide domain; or based on a peptoid such as a vinylogous peptoid. Where the agent is a small organic molecule such as a steroidal alkaloid (e.g., cyclopamine), it can be administered in a form that releases the active agent at the desired position in the body (e.g., the stomach), or by injection into a blood vessel that the agent circulates to the target cells (e.g., hematopoietic malignancy cells).

Regardless of the route of administration selected, the compounds of the present invention, which may be used in a suitable hydrated form, and/or the pharmaceutical compositions of the present invention, are formulated into pharmaceutically acceptable dosage forms such as described herein or by other conventional methods known to those of skill in the art.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of agent to increase insulin expression or reduce lipotoxicity a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day which can be administered in single or multiple doses.

If desired, the effective daily dose of the active compound may be administered as two, three, four, five, six or more sub-doses administered separately at appropriate intervals throughout the day, optionally, in unit dosage forms. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Additionally, in various aspects, a physician or veterinarian having ordinary skill in the art can readily determine an appropriate subject for administration of the compounds described herein. For example, one of skill in the art is capable of routine diagnosis of diabetes. Also, it is routine for one of skill in the art to determine the appropriate compounds to be administered to the subject as well as the timing of administration depending on the diagnosis (e.g., Type I or Type II diabetes, hypoglycemic, insulin resistant, and the like). For example, it may be appropriate to administer a compound that increases insulin production with or without exogenous insulin to a patient experiencing low insulin levels. Additionally, it may be appropriate to administer the compound in combination with other drugs.

When other therapeutic agents are employed in combination with the compounds of the present invention they may be used for example in amounts as noted in the Physician Desk Reference (PDR) or as otherwise determined by one having ordinary skill in the art.

The term "effective amount" is defined as the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality. For example, a "therapeutically effective amount" of, e.g., an insulin activator, with respect to the subject method of treatment, refers to an amount of the compound in a preparation which, when applied as part of a desired dosage regimen brings about, e.g., a change in insulin production according to clinically acceptable standards for the disorder to be treated.

The following examples are intended to illustrate but not limit the invention.

Example 1

High Throughput Screening Assay for Identification of Agents that Activate β-Cell Differentiation Of Progenitor Cells A high throughput screening (HTS) assay was developed to identify agents that activate β-cell differentiation from adult non-endocrine cells.

Based on the observation that PDX-1 is implicated in the role of β-cell maturation as shown in FIG. 5, promoter/reporter constructs were developed as shown in FIG. 6 to detect the effect of candidate agents on PDX-1 promoter activation. The viral vector constructs were used to infect cultured NEPCs which were then contacted with various test agents and analyzed to detect changes in expression activity of the reporter.

Figures 8A, 8B:
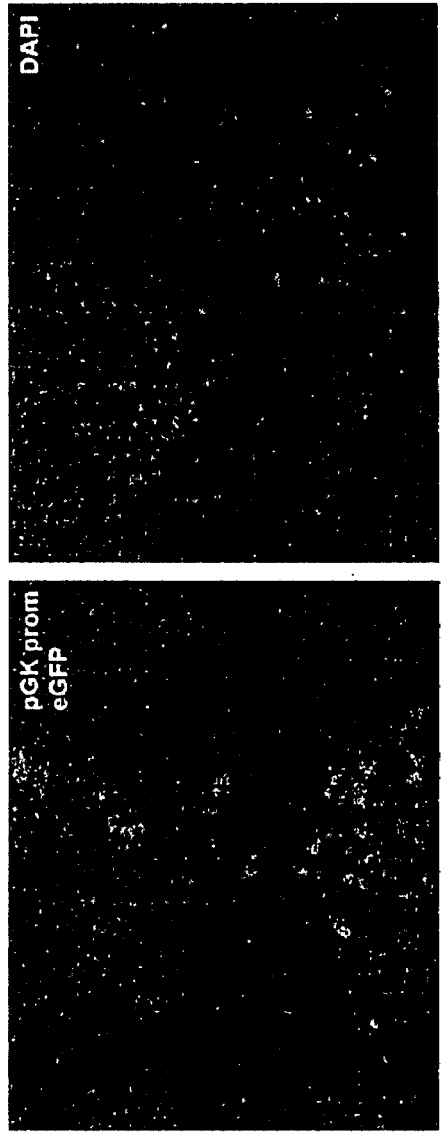
FIG. 8 shows a pictorial representation of NEPCs infected in suspension with viral vector constructs followed by plating directly into assay plates and cultured for four days before image analysis using fluorescence microscopy with detection of eGFP (FIG. 8A) and fluorescent staining with DAPI (FIG. 8B).
Figure 13:
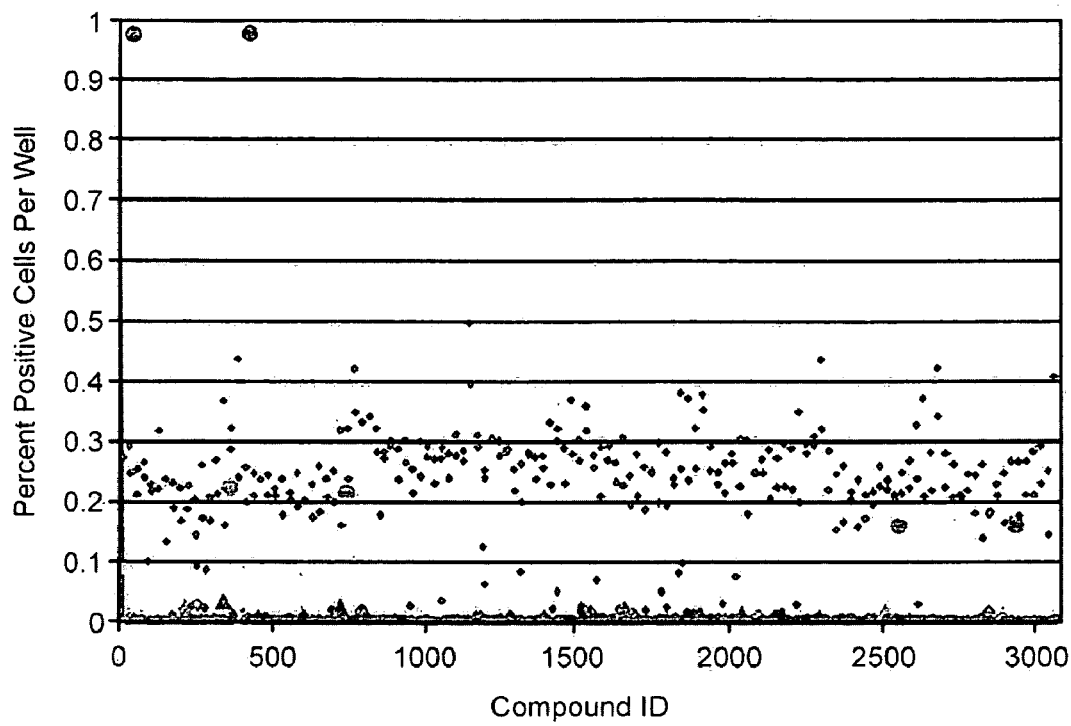
FIG. 13 shows a graphical representation of screening results for identification of regulators of insulin gene transcription.
Figure 14:
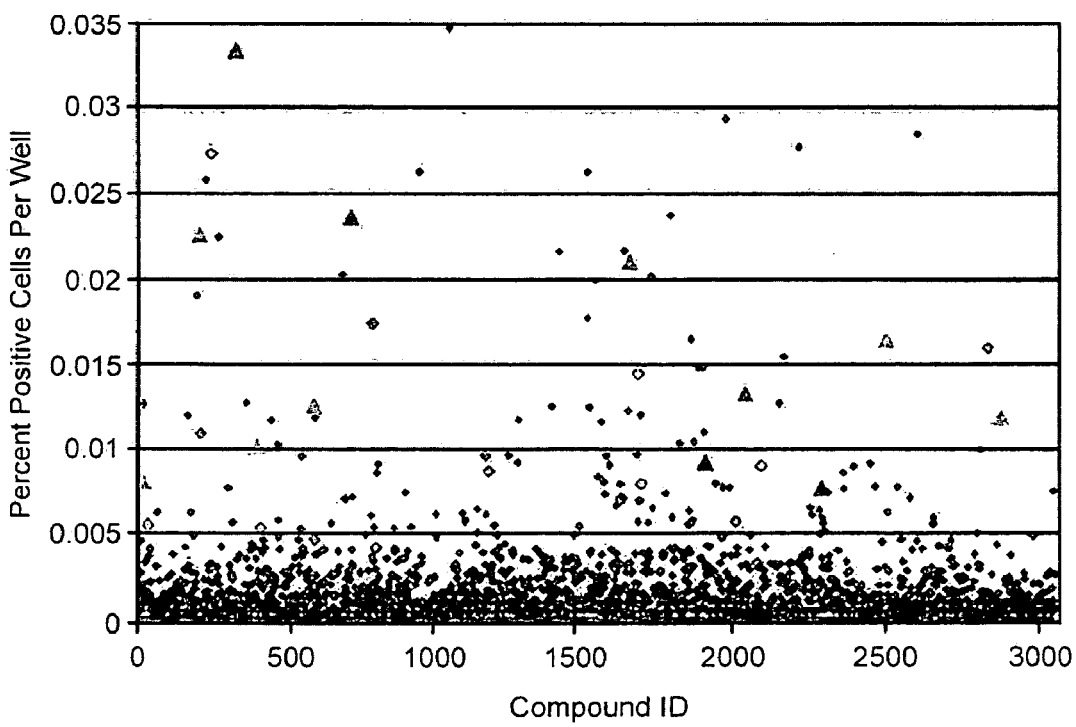
FIG. 14 shows a graphical representation of screening results for identification of regulators of insulin gene transcription.

Cell culturing was adapted to 384-well microtiter plate format to facilitate HTS. Additionally, infection of the NEPCs was optimized to maximize infection efficiency and cell survival. Infection of NEPCs in suspension followed by plating directly into 384-well microtiter plates coated with Collagen I improved cell survival and optimized infection efficiency. FIG. 8 shows NEPCs infected in suspension with viral vectors including pGK promoter/eGFP constructs. The cells were directly plated on Collagen I coated assay plates and grown for 4 days before performing image analysis. In contrast, FIGS. 9 and 10 show NEPCs in which the cells were plated on Collagen I coated plates and grown for 3.5 days (FIGS. 9A and 10A) and subsequently replated and grown for an additional day (FIGS. 9B and 10B). A dramatic decrease in cell survival is associated with replating of the cell.

The plating media was supplemented with 10% plasma which was shown to improve monolayer formation in the 384-well Collagen I coated microtiter plates as shown in FIG. 11B (with plasma) as compared with FIG. 11A (without plasma).

A library of 1000 candidate drug compounds was initially screened using NEPCs cultured in a 384-well HTS format using the following method. NEPCs were infected with promoter/reporter constructs in suspension for 6 hours. The cells were then directly plated on Collagen I coated 384-well microtiter plates in media containing 10% plasma. Monolayer formation was allowed to progress by culture for 4 days with regular media changes. Library compounds were then contacted with the cells and added at a final concentration of 5 μM and incubated for 48 hours. Image analysis was then performed using fluorescent microscopy using DAPI to fix the cells and imaging of GFP to determine promoter activation activity of individual compounds. Image analysis algorithms are further refined to eliminate auto-fluorescent debris to accurately quantify green fluorescence.

Preliminary results of the initial screening of the original 1000 candidate compound library is shown in FIG. 12. The level of green intensity of individual compounds is indicative of promoter activation by individual compounds.

Example 2

High Throughput Screening Approach to β-Cell Replacement and Maintenance

A multi-tiered approach has been developed incorporating HTS assays to identify both novel regulators of insulin gene transcription and lipotoxicity reversal.

The assays employ a cell line derived from human fetal islet cells (T6PNE) in which the cells are infected with a promoter/reporter construct. The construct is shown in FIG. 7 and incorporates an insulin promoter operably linked to an eGFP. Cells were infected and plated, and candidate libraries screened and "hit" detected as discussed in Example 1.

To differentiate between agents that specifically act to reverse lipotoxicity as compared to generally increasing transcription of insulin a two layer screening approach was utilized. In the first layer, islet cells infected with an insulin promoter/reporter construct are screened in the absence of a fatty acid. A "hit" indicates an agent that is capable of increasing insulin transcription. In the second layer, islet cells infected with an insulin promoter/reporter construct are screened in the presence of a fatty acid. A "hit" indicates a drug that reverses the effects of the fatty acid addition, for example reduction of insulin transcription. This drugs screened in both layers may be used to identify whether the drug is specific to lipotoxicity reversal. For example, drugs that are "hits" in the second layer screen but not in the first layer screen are specific to lipotoxicity reversal.

Figure 15:
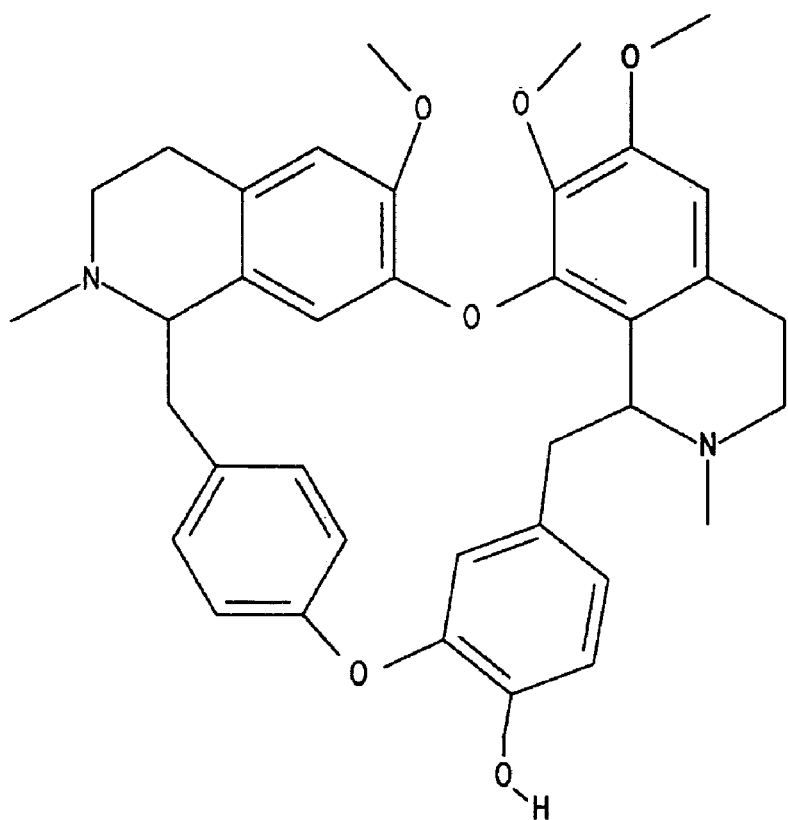
FIG. 15 shows a pictorial representation of the chemical structure of berbamine.
Figure 16:
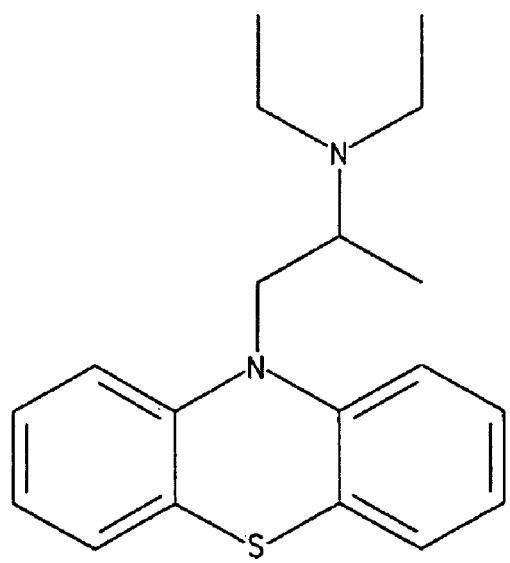
FIG. 16 shows a pictorial representation of the chemical structure of ethopropazine.

In addition to the screening procedure described in Example 1, additional confirmatory assays were conducted as described above to identify agents capable of reducing lipotoxicity. A first layer screen of a library of the 1000 candidate agents was performed to identify regulators of insulin gene transcription. The results showing "hits" from the first round of screening is shown in FIGS. 15 and 16. Approximately 30 compounds were selected as positive "hits" with estrogen analogs and auto-fluorescent drugs being eliminated.

Figure 17:
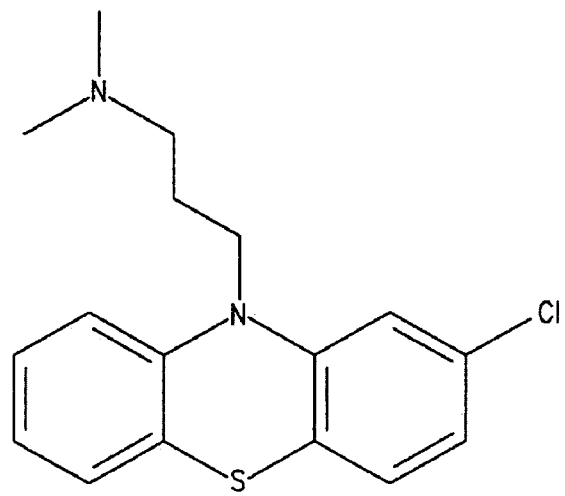
FIG. 17 shows a pictorial representation of the chemical structure of chlorpromazine.

A confirmatory screen was then performed which was a repeat of the initial screen with dose response using the identified compounds. Three of the originally identified activators were confirmed in this round. The activators included berbamine (FIG. 15), ethopropazine (FIG. 16) and chlorpromazine (FIG. 17).

Figure 18:
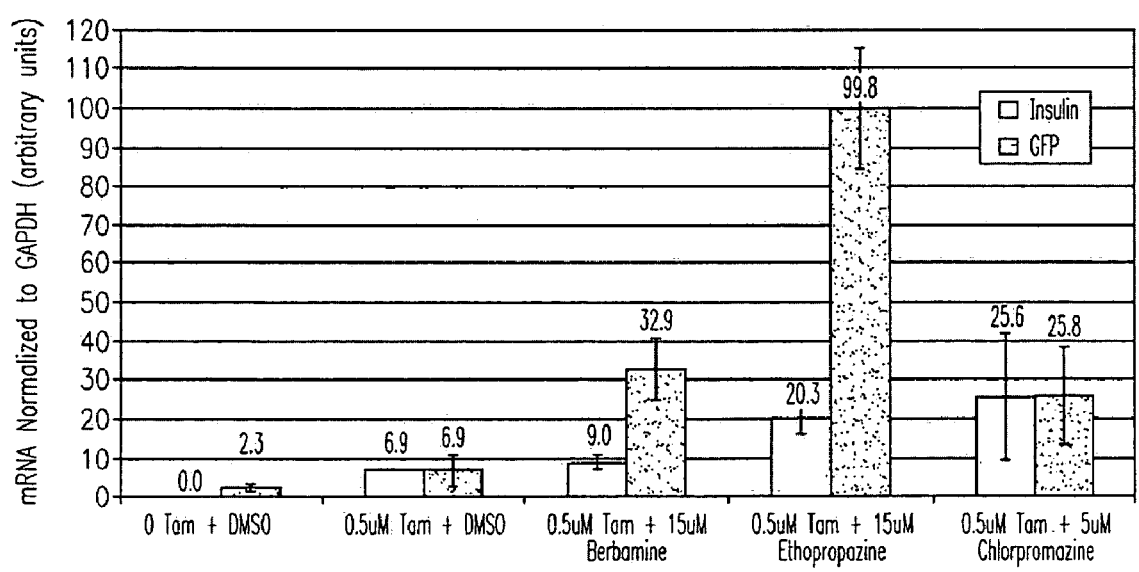
FIG. 18 shows a graphical representation of screening results for identification of regulators of insulin gene transcription. The left block of each histogram set shows endogenous insulin while the right block of each set shows GFP reporter driven by an insulin promoter.

A secondary round was performed in which the identified compounds were screened to measure endogenous insulin transcription in the presence of the identified activators. The results are shown in FIG. 18 which shows that all 3 identified compounds activated endogenous insulin transcription as well as increased expression of GFP through activation of an insulin promoter.

Figure 19:
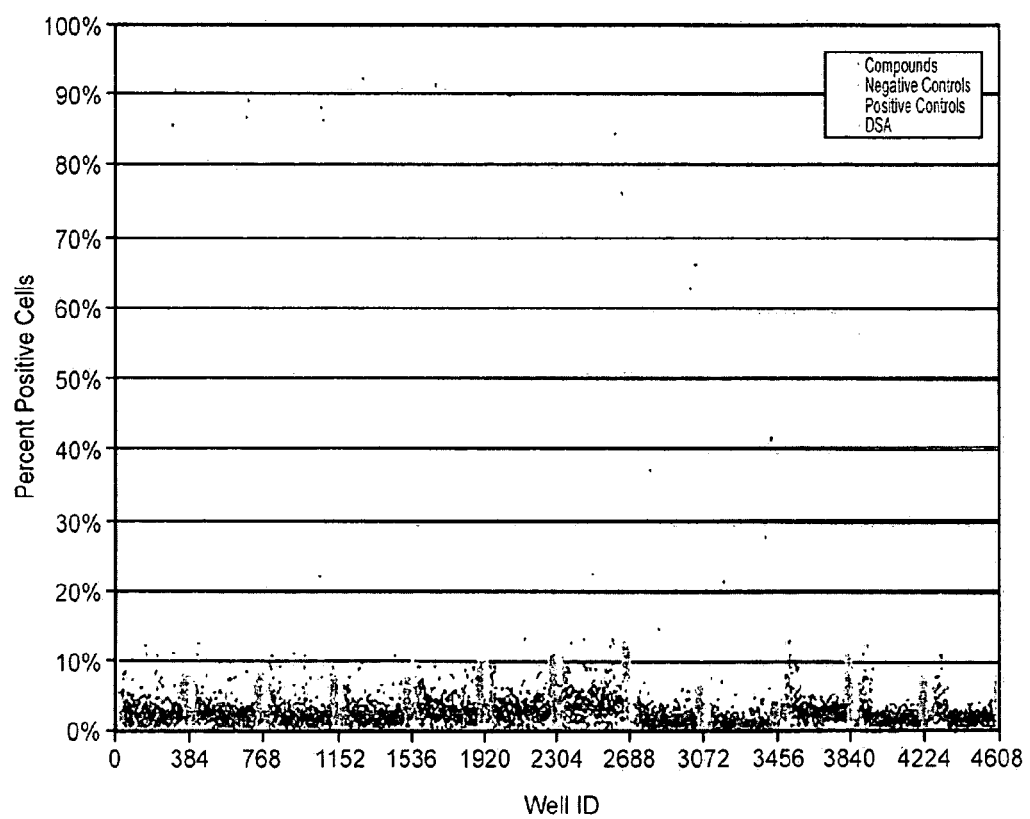
FIG. 19 shows a graphical representation of screening results for identification of regulators of insulin gene transcription not in the presence of a fatty acid.
Figure 20:
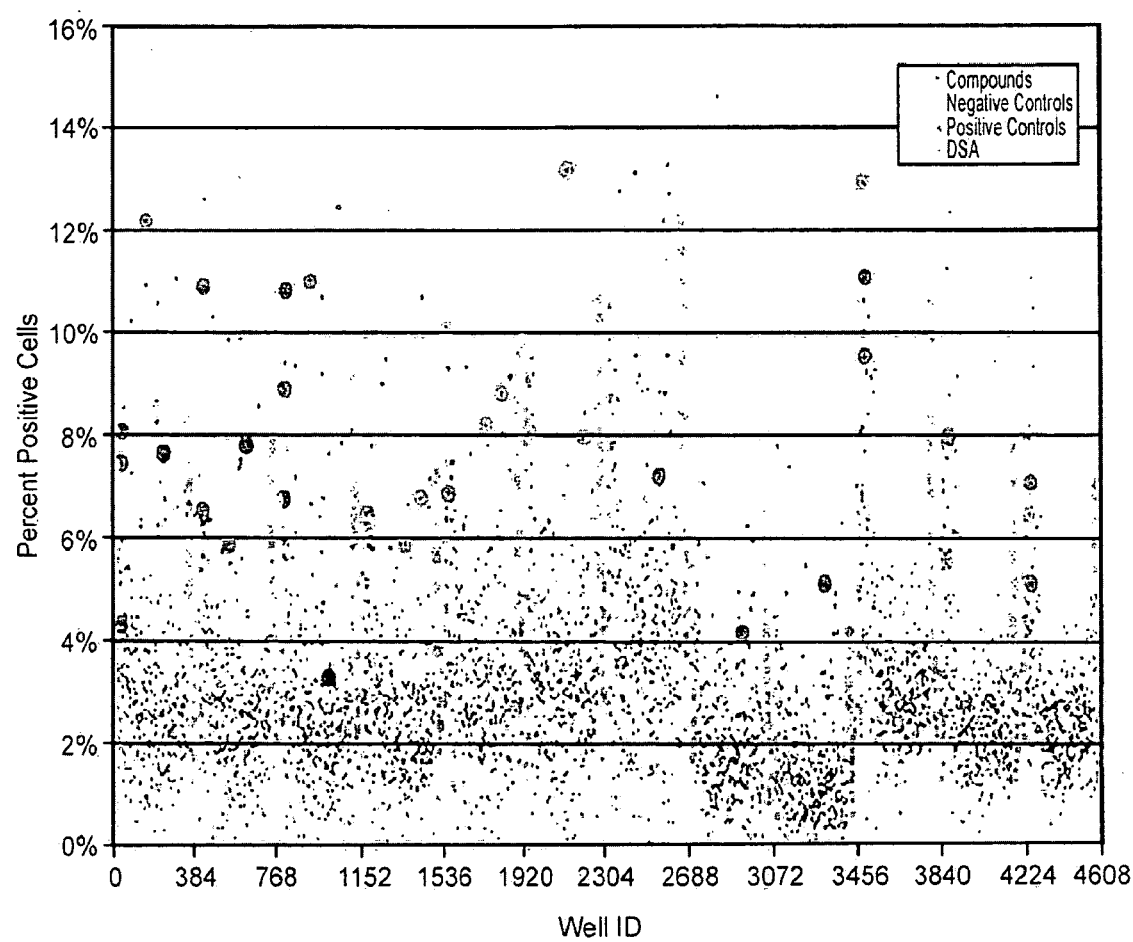
FIG. 20 shows a graphical representation of screening results for identification of regulators of insulin gene transcription in the presence of a fatty acid.

The compound library was then screened to identify compounds capable of reversing palmitate-induced lipotoxicity. The results of the screen performed not in the presence of a fatty acid are shown in FIG. 19 and the results of the screen performed in the presence of a fatty acid are shown in FIG. 20. From analysis of the results, specific drug classes were represented by individual drugs shown to reverse palmitate-induced lipotoxicity. The following classes of drugs were represented and are expected to reverse lipotoxicity: fatty acid metabolism modulator drugs, anti-inflammatory drugs, and antioxidants. Specific drugs that affect fatty acid metabolism modulators which are expected to reverse lipotoxicity are lovastatin, a HMGCoA reductase inhibitor and benfluorex hydrochloride, a beta-oxidation inhibitor. Specific anti-inflammatory drugs which are expected to reverse lipotoxicity are triamcinolone acetonide, a corticosteroid; dexamethasone acetate, a glucocorticoid; and mefenamic acid, a non-steroidal which inhibits prostaglandin synthesis. Specific antioxidants which are expected to reverse lipotoxicity include beta-carotene, and alpha-tocopheryl acetate. Other classes of drugs expected to reverse lipotoxicity are neuroleptics/cholinergics/adrenergics, antitussives, antibiotics, and antiarrhythmics. For example, cloperastine hydrochloride and ipratropium bromide monohydrate are expected to reverse lipotoxicity.

Example 3

High Throughput Screening of the ChemBridge Diver Set™ Compound Library

Figure 21:
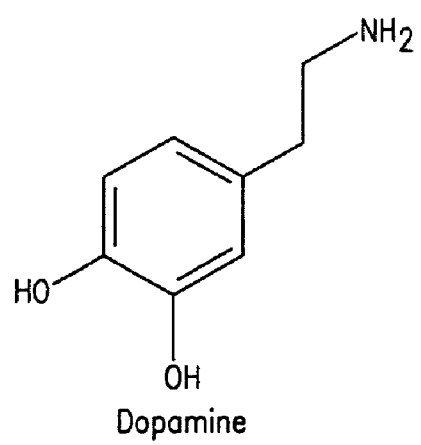
FIG. 21 shows a pictorial representation of the chemical structures of dopamine.

The ChemBridge DiverSet™ library of compounds was screened as discussed in Example 2. The results of the screen identified one compound that upregulated the insulin promoter, dopamine (FIG. 21).

Figure 22:
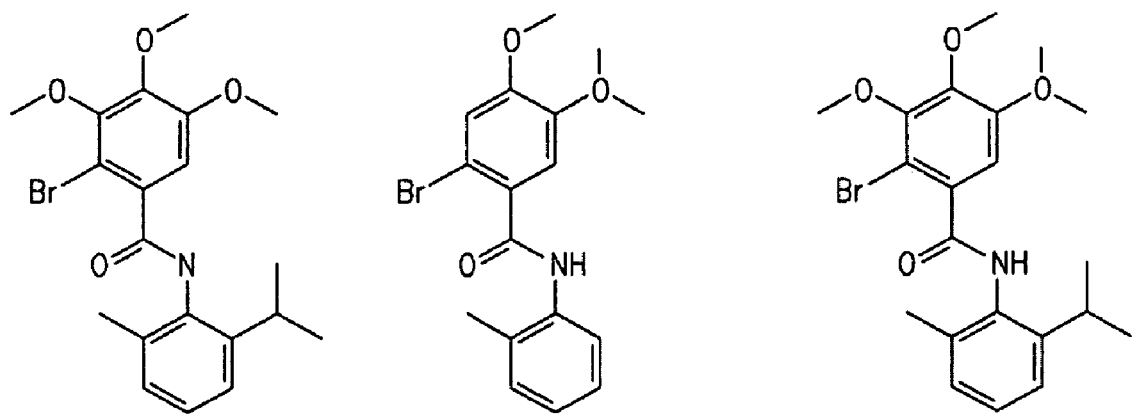
FIG. 22 shows a pictorial representation of the chemical structures of known dopamine agonists. The two structure on the left are overlaid and displayed as a composite structure on the right.

Chemi-informatic analysis revealed structural similarities to a known dopamine agonist. Similarities between known dopamine agonists are shown in FIG. 22. Accordingly, it is expected that dopamine agonists reverse lipotoxicity.

Example 4

Role of Neurotransmitter Receptors in β-Cell Function

Dopamine (D2), Glutamine (Kainate, NMDA, and AMPA) and Cholinergic (M3) receptor subtypes are present on the β-cell. They are all known to play a role in modulating insulin secretion. However, there has previously been no data linking these receptors to insulin promoter activity. Accordingly, a core emphasis of the current research was to determine the receptor subtypes being stimulated by the screening methods described herein and how these receptors are linked to the insulin promoter.

Figure 23:
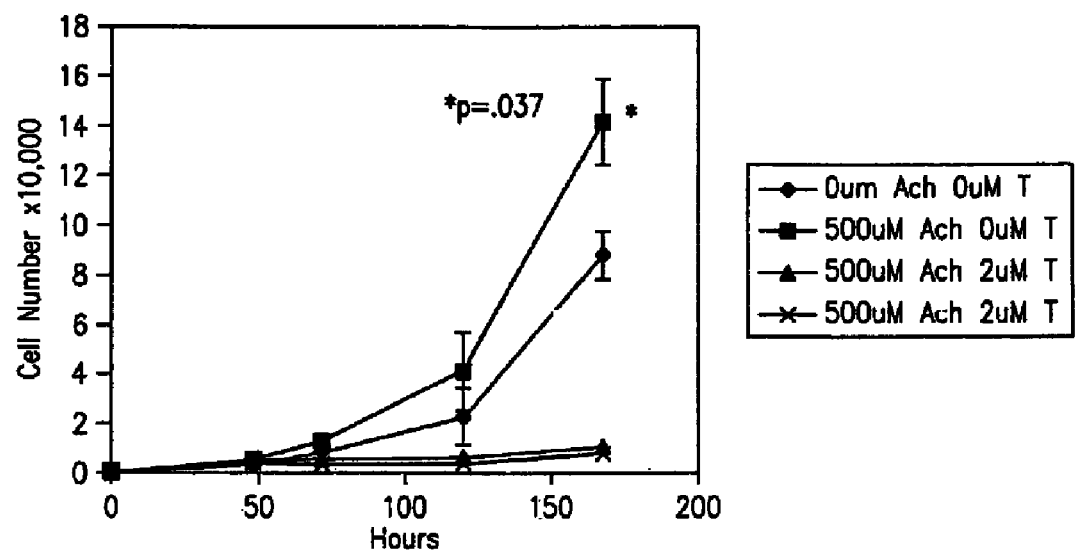
FIG. 23 shows a graphical representation of the proliferation of islet cells by administration of acetylcholine.

Cholinergic receptors play roles in proliferation and function of islet cells. For example, it has been determined that acetylcholine stimulates proliferation of β-cells as shown in FIG. 23. Muscarinic receptors (M3) are generally known to control cell growth in diverse physiological situations. It has been determined that M3 receptors are expressed in β-cells and are well known to regulate insulin secretion. Additionally, there are data indicating the cholinergic innervation of islets regulates β-cell proliferation.

Example 5

Mechanisms of Replication in the Human Pancreas

Figure 24:
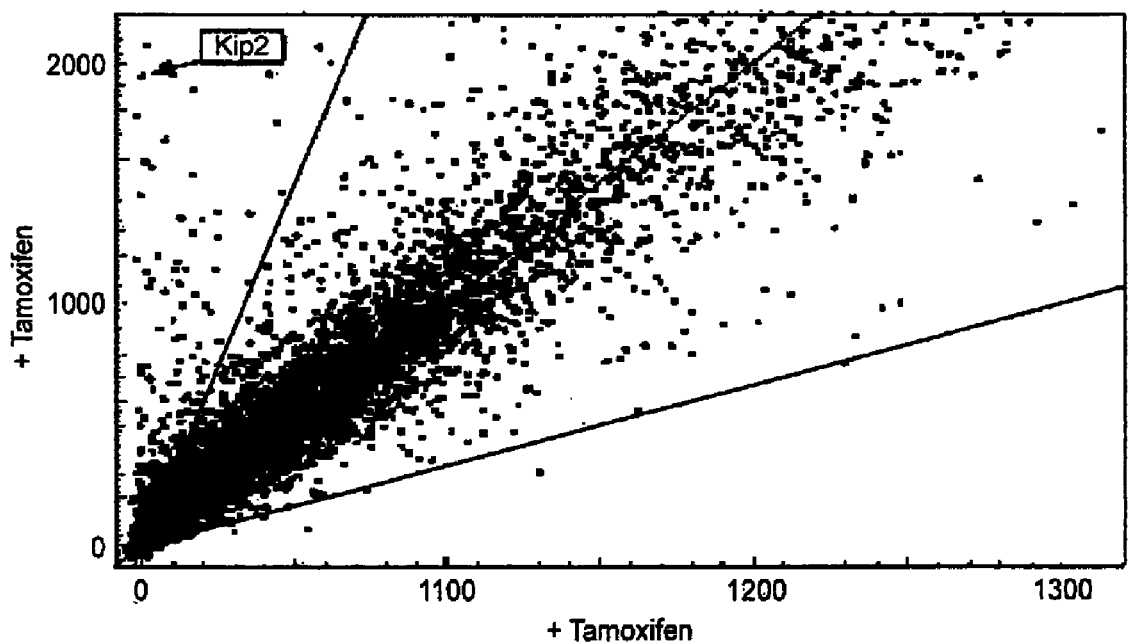
FIG. 24 shows a graphical representation of Illumina™ gene array data showing 2000 fold induction of Kip2/p57 by E47.
Figure 25:
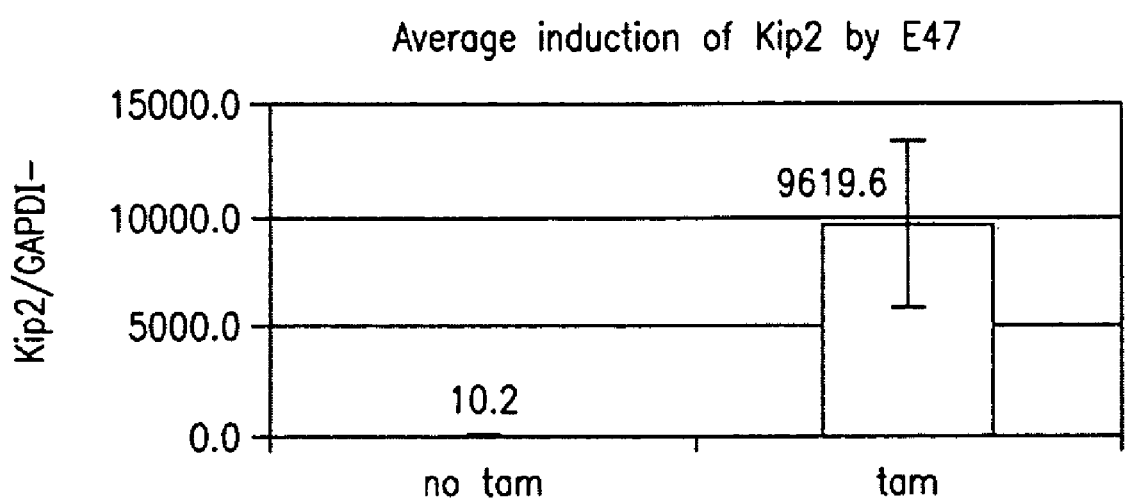
FIG. 25 shows a graphical representation of quantitative PCR showing 1000 fold induction of Kip2/p57 by E47.

It was first determined that tamoxifen induction of E47 causes growth arrest in T6PNE cells. Kip2/p57 is highly induced by E47 (plus tamoxifen) in T6PNE cells and required for cell cycle arrest by E47. As shown in assays performed using Illumina™ gene arrays a 2000 fold induction is observed with E47/tamoxifen (FIG. 24). Additionally, quantitative PCR confirms a 1000 fold induction (FIG. 25).

Kip2 is the major CDKi in human islets, but not in rodents. A loss of Kip2 is associated with hyperinsulemic hypoglycemia of childhood, in which β-cells proliferate aberrantly and exhibit constitutive insulin secretion.

Figure 26:
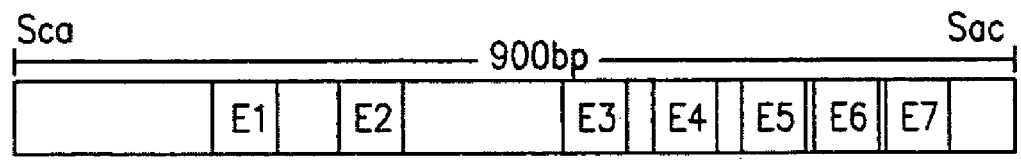
FIG. 26 shows a pictorial representation of the Sca to Sac region of the Kip2 gene promoter.

The Kip2 promoter has been determined to be responsive to E47. The E boxes within the Sac to Sca region of the promoter were identified. FIG. 26 shows the Sac to Sca region including E boxes. Subsequent CHIP™ analysis detected E47 bound to the E2 element.

Figure 27:
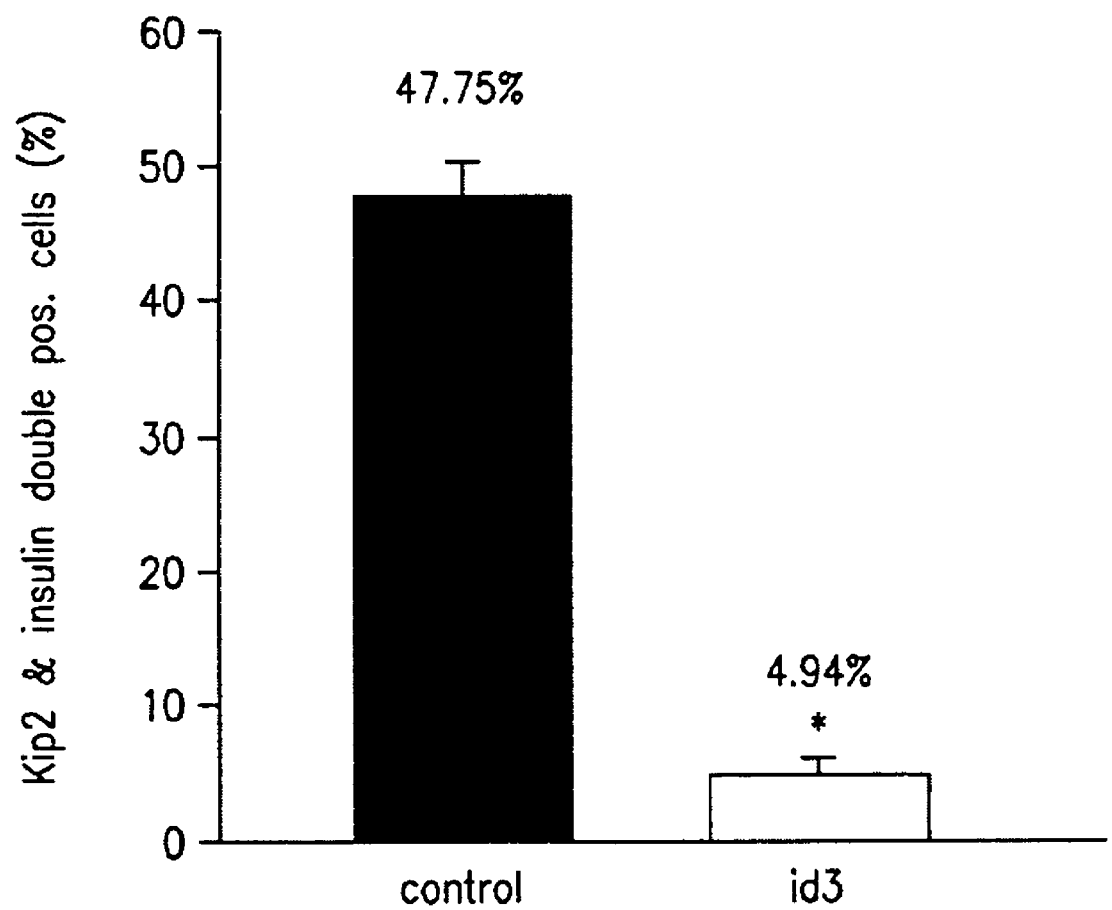
FIG. 27 shows a graphical representation of the percentage of adult β-cells infected with constructs expressing Id3 producing insulin and Kip2 as compared to non-infected cells.
Figure 28:
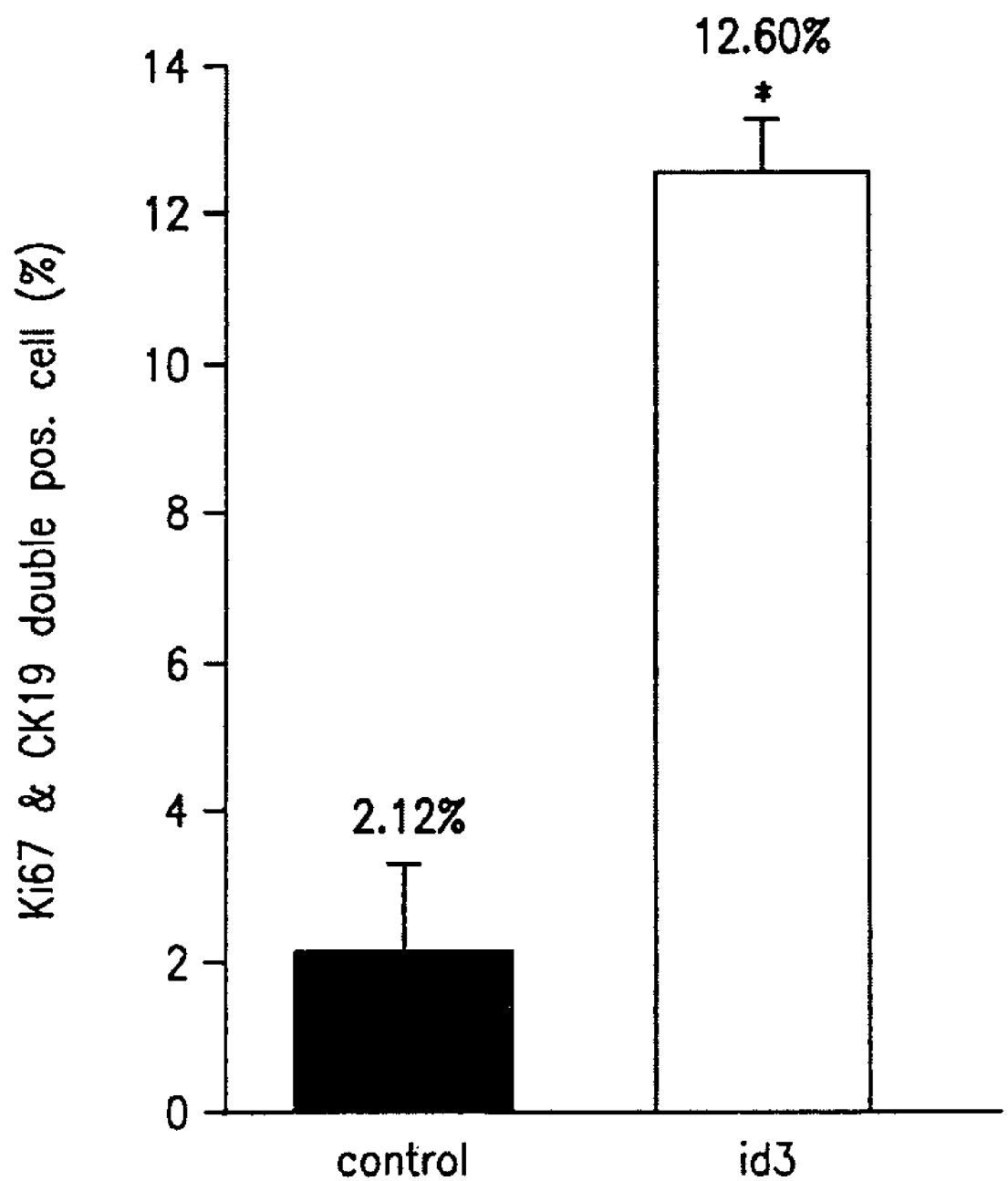
FIG. 28 shows a graphical representation of cells infected with constructs expressing Id3 which are positive for both Ki67 and CK19 (markers for cell proliferation), as compared to non-infected cells.
Figure 29:
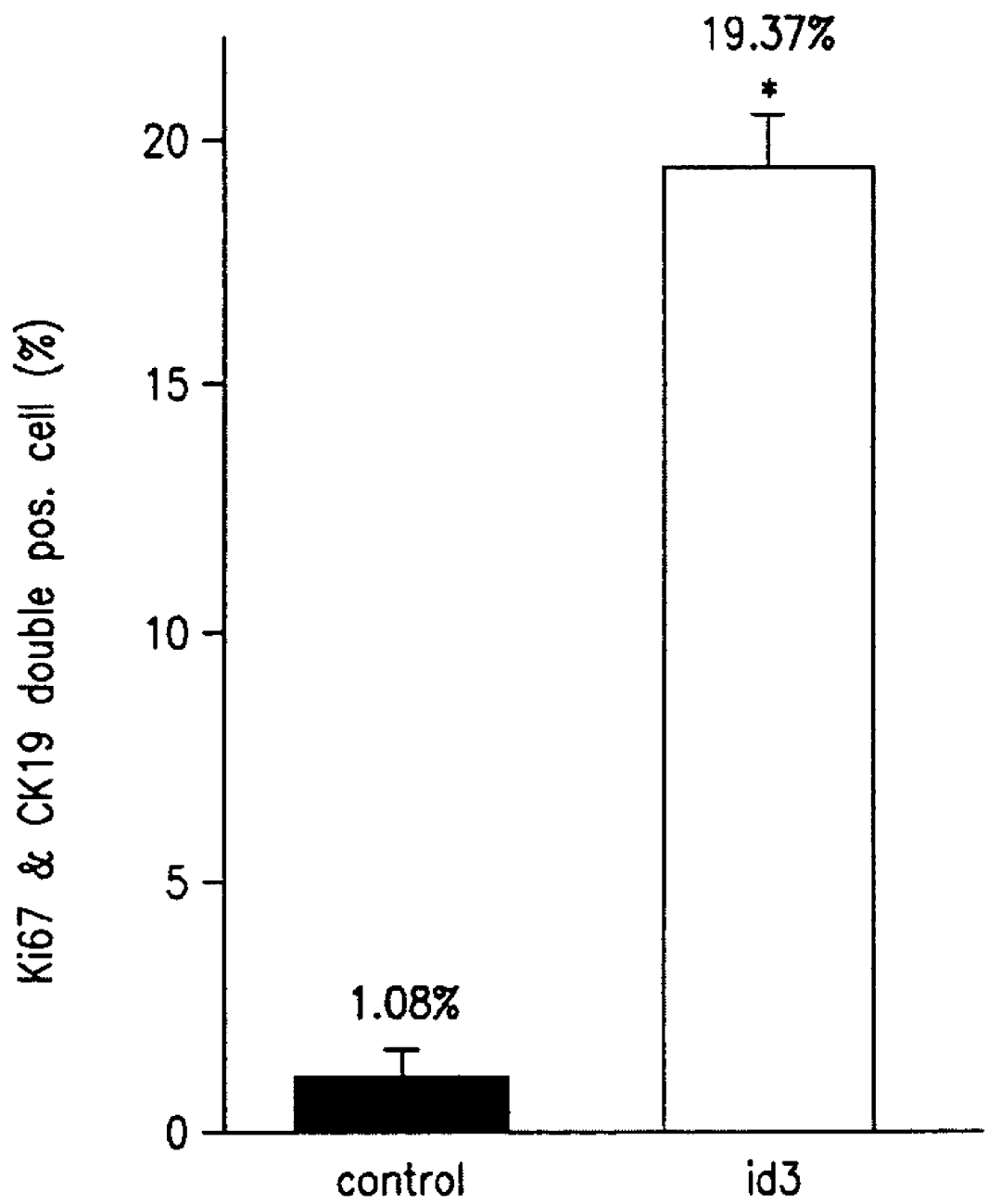
FIG. 29 shows a graphical representation cells infected with constructs expressing Id3 which are positive for both Ki67 and CK19 (markers for cell proliferation), as compared to non-infected cells.
Figure 30:
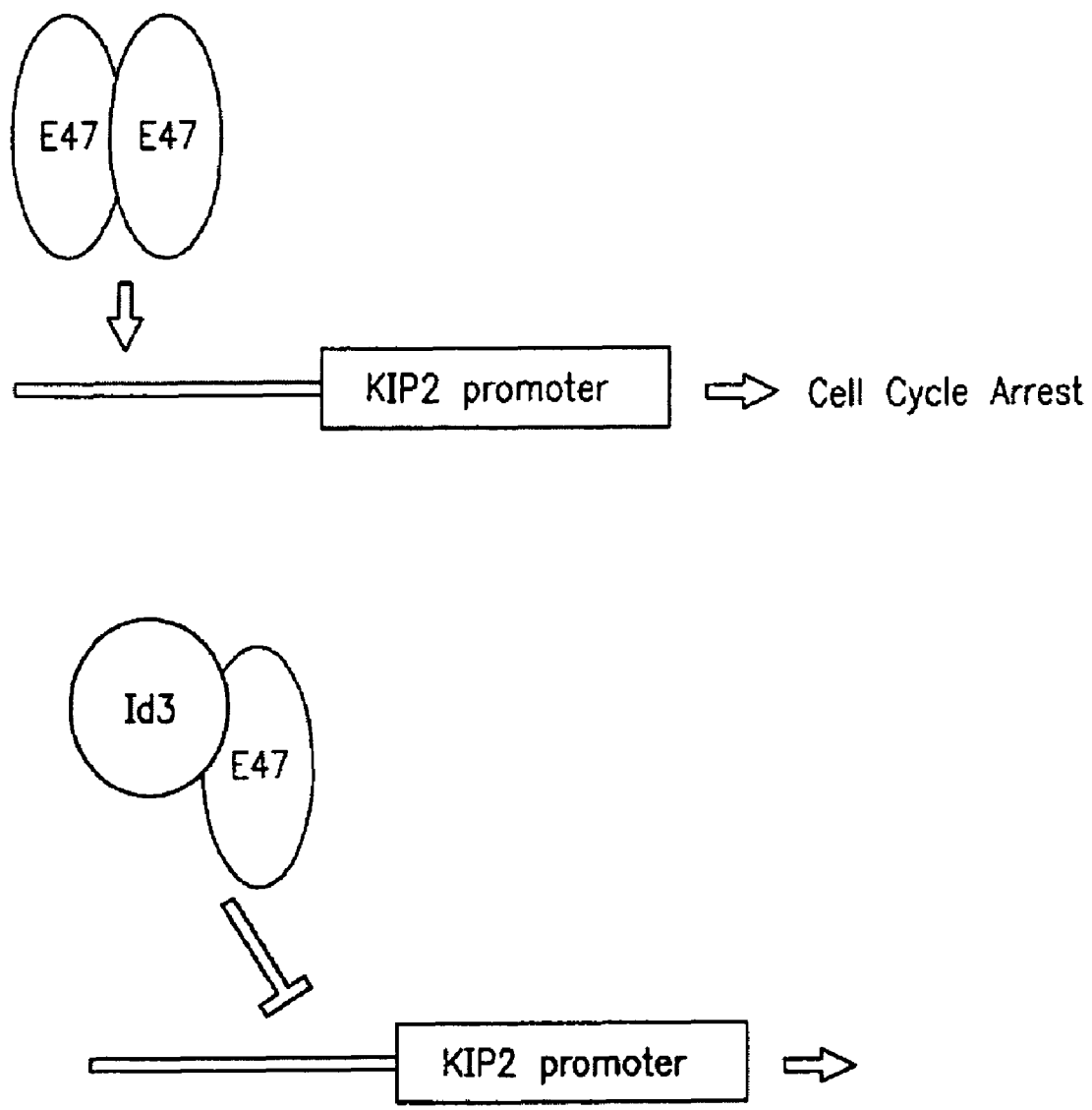
FIG. 30 shows a pictorial representation of the regulation Kip2 promoter induction.

A further revelation of the mechanism of Kip2 activation was determined. Id3 was determined to inhibit Kip2 in adult β-cells. For example in adult β-cells infected with constructs expressing Id3, the percentage of cells producing insulin and Kip2 as compared to non infected cells was drastically reduced as shown in FIG. 27. Additionally, Id3 has been shown to induce replication of adult duct cells as shown in FIG. 28, which shows an increase in the percentage of cells infected with constructs expressing Id3 which are positive for both Ki67 and CK19, (markers for cell proliferation) as compared to non-infected cells. Similarly, Id3 has been shown to induce replication of fetal duct cells in a similar manner as shown in FIG. 29. Finally, Id3 was determined to induce PDX-1 in fetal pancreas cells. Fetal cells infected with constructs expressing Id3, showed an increase in PDX-1.

In summary, Id3 has been shown to induce replication in duct cells in adult and fetal pancreas. Id3 also down regulates Kip2 in adult β-cells. With regard to Id3 regulation of neogenesis, Id3 has been shown to activate PDX-1 in fetal pancreas cells.

Although the invention has been described with reference to the above example, it will be understood that modifications and variations are encompassed within the spirit and scope of the invention. Accordingly, the invention is limited only by the following claims.

What is claimed is:

1. A method of screening for an agent that reduces lipotoxicity in a subject having Type I or Type II diabetes comprising:
    a) transfecting a cell with a vector comprising an insulin promoter operably linked to a nucleic acid encoding a reporter protein, wherein the reporter protein is a fluorescent protein;
    b) contacting the cell with a candidate agent; and
    c) detecting the reporter protein, thereby identifying an agent that reduces lipotoxicity.

2. The method of claim 1, where the cell is derived from a human fetal islet cell.

3. The method of claim 1, wherein the cell is further contacted with a fatty acid.

4. The method of claim 3, wherein the fatty acid is palmitate.

5. The method of claim 1, wherein the subject is a human.

6. The method of claim 1, wherein the cell is transfected in solution and then cultured in a microtiter plate.

7. The method of claim 6, wherein the cells are culture 4 days before detection.

8. The method of claim 1, wherein the fluorescent protein is green fluorescent protein (GFP) or enhanced green fluorescent protein (eGFP).

9. The method of claim 1, wherein detection of the reporter protein is performed using fluorescence microscopy.

10. The method of claim 1, wherein the screening is performed in a high throughput format.

11. A method of screening for an agent that reduce lipotoxicity in a subject having Type I or Type II diabetes comprising:
    a) transfecting a cell with a vector comprising an insulin promoter operably linked to a nucleic acid encoding a reporter protein, wherein the reporter protein is green fluorescent protein (GFP) or enhanced green fluorescent protein (eGFP);
    b) contacting the cell with a candidate agent; and
    c) detecting the reporter protein, thereby identifying an agent that reduces lipotoxicity.

* * * * *